US012059412B2

(12) United States Patent
Choi et al.

(10) Patent No.: US 12,059,412 B2
(45) Date of Patent: Aug. 13, 2024

(54) PHARMACEUTICAL COMPOSITION CONTAINING (R)-N-[1-(3,5-DIFLUORO-4-METHANE-SULFONYLAMINO-PHENYL)-ETHYL]-3-(2-PROPYL-6-TRIFLUOROMETHYL-PYRIDIN-3-YL)-ACRYLAMIDE AND METHOD FOR INHIBITING CRYSTAL FORMATION THEREOF

(71) Applicant: Amorepacific Corporation, Seoul (KR)

(72) Inventors: Joonho Choi, Yongin-si (KR); Wonkyung Cho, Yongin-si (KR); Jong Hwa Roh, Yongin-si (KR); Kwanghyun Shin, Yongin-si (KR); Byoung Young Woo, Yongin-si (KR); Min Soo Kim, Yongin-si (KR); Miyoung Park, Yongin-si (KR); Youngho Park, Yongin-si (KR); Eunsil Park, Yongin-si (KR); Jaehong Park, Yongin-si (KR); Kiwha Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 161 days.

(21) Appl. No.: 16/976,140

(22) PCT Filed: Mar. 21, 2019

(86) PCT No.: PCT/KR2019/003297
§ 371 (c)(1),
(2) Date: Aug. 27, 2020

(87) PCT Pub. No.: WO2019/203461
PCT Pub. Date: Oct. 24, 2019

(65) Prior Publication Data
US 2020/0405701 A1 Dec. 31, 2020

(30) Foreign Application Priority Data
Apr. 18, 2018 (KR) .................. 10-2018-0044818

(51) Int. Cl.
*A61K 31/44* (2006.01)
*A61K 9/00* (2006.01)
*A61K 31/79* (2006.01)
*A61K 47/32* (2006.01)

(52) U.S. Cl.
CPC ............ *A61K 31/44* (2013.01); *A61K 9/0014* (2013.01); *A61K 47/32* (2013.01)

(58) Field of Classification Search
CPC ...... A61K 31/44; A61K 9/0014; A61K 47/32; A61K 31/79
See application file for complete search history.

(56) References Cited

U.S. PATENT DOCUMENTS

| | | | |
|---|---|---|---|
| 5,942,501 A | 8/1999 | Hayward et al. | |
| 2007/0249692 A1 | 10/2007 | Fort et al. | |
| 2008/0194638 A1 | 8/2008 | Dedhiya et al. | |
| 2008/0312234 A1 * | 12/2008 | Kim ...................... | A61P 27/02 544/131 |
| 2009/0099189 A1 | 4/2009 | Ulven et al. | |
| 2010/0047297 A1 | 2/2010 | Petersen | |
| 2012/0196875 A1 | 8/2012 | Bouyssou et al. | |
| 2012/0295935 A1 | 11/2012 | Frid et al. | |
| 2013/0184290 A1 | 7/2013 | Padval et al. | |
| 2014/0024693 A1 | 1/2014 | Malhotra et al. | |

FOREIGN PATENT DOCUMENTS

| | | | |
|---|---|---|---|
| JP | 2000-256167 A | 9/2000 | |
| JP | 2008-519817 A | 6/2008 | |
| KR | 10-2007-0045153 A | 5/2007 | |
| KR | 10-2012-0032459 A | 4/2012 | |
| KR | 10-1410318 B1 | 6/2014 | |
| KR | 10-2016-0101554 A | 8/2016 | |
| KR | 10-2017-0081315 A | 7/2017 | |
| WO | 01/42222 A1 | 6/2001 | |
| WO | 02/064543 A2 | 8/2002 | |
| WO | 2006/064283 A1 | 6/2006 | |
| WO | 2008/013414 A1 | 1/2008 | |
| WO | 2008/074413 A2 | 6/2008 | |
| WO | WO-2010092355 A2 * | 8/2010 | ............ A01N 25/02 |
| WO | 2011/054436 A2 | 5/2011 | |
| WO | 2012/013567 A1 | 2/2012 | |
| WO | 2012/150952 A1 | 11/2012 | |
| WO | 2014/057003 A1 | 4/2014 | |
| WO | 2014/133196 A1 | 9/2014 | |

(Continued)

OTHER PUBLICATIONS

Haaf, F., A. Sanner and F. Straub, "Polymers of N-Vinylpyrrolidone: Synthesis, Characterization and Uses", Polymer Journal (1985), 17 (1), pp. 143-152. (Year: 1985).*
Kim, J. and H. Choi, "Effect of additives on the crystallization and the permeation of ketoprofen from adhesive matrix", International Journal of Pharmaceutics (2002), 236: pp. 81-85. (Year: 2002).*
Tian et al., "A comparison of the effect of temperature and moisture on the solid dispersions: Aging and crystallization", International Journal of Pharmaceutics, 2014, vol. 475, pp. 385-392 (total 8 pages).
Soliman et al., "Preparation of celecoxib solid dispersions for dermal application: in vitro characterization and skin irritation test", J. Drug Del. Sci. Tech., 2011, vol. 21, No. 6, pp. 509-516 (total 8 pages).

(Continued)

*Primary Examiner* — Amanda L. Aguirre
*Assistant Examiner* — Sagar Patel
(74) *Attorney, Agent, or Firm* — Sughrue Mion, PLLC (57) ABSTRACT

One aspect of the present disclosure relates to a pharmaceutical composition, containing (R)-N-[1-(3,5-difluoro-4-methanesulfonylamino-phenyl)-ethyl]-3-(2-propyl-6-trifluoromethyl-pyridin-3-yl)-acrylamide as a first ingredient and containing a vinylpyrrolidone-based polymer as a second ingredient. The composition of one aspect of the present disclosure has a formulation characteristic in which the crystal formation of a compound represented by chemical formula 1 is delayed for a long time.

10 Claims, 5 Drawing Sheets

(56) References Cited

FOREIGN PATENT DOCUMENTS

WO 2015/066584 A1 5/2015

OTHER PUBLICATIONS

Isengard et al., "'Hidden parameters' of infrared drying for determining low water contents in instant powders", Talanta, 1999, vol. 50, pp. 239-246 (total 8 pages).
Horozov et al., "Stability of Suspensions, Emulsions, and Foams Studied by a Novel Automated Analyzer", Langmuir, 2004. vol. 20, pp. 9007-9013 (total 7 pages).
Celia et al., "Long Term Stability Evaluation of Prostacyclin Released from Biomedical Device Through Turbiscan Lab Expert", Medicinal Chemistry, 2015, vol. 11, pp. 391-399 (total 9 pages).
Yun et al., "TRPV1 antagonist can suppress the atopic dermatitis-like symptoms by accelerating skin barrier recovery", Journal of Dermatological Science, 2011, vol. 62, pp. 8-15 (total 8 pages).
Lim et al., "Development of PAC-14028, a Novel Transient Receptor Potential Vanilloid Type 1 (TRPV1) Channel Antagonist as a New Drug for Refractory Skin Diseases", Arch Pharm Res, 2012, vol. 35, No. 3, pp. 393-396 (total 4 pages).
Park et al., "Oral and topical pharmacokinetic studies of a novel TRPV1 antagonist, PAC-14028 in rats and minipigs using liquid chromatography/tandem mass spectrometric method", Journal of Pharmaceutical Biomedical Analysis, 2012, vol. 61, pp. 8-14 (total 7 pages).
Shaw et al., "The Effect of Selected Water-Soluble Excipients on the Dissolution of Paracetamol and Ibuprofen", Drug Development and Industrial Pharmacy, 2005, vol. 31, pp. 515-525 (total 11 pages).
International Search Report for PCT/KR2019/003297 dated Jun. 24, 2019 [PCT/ISA/210].
Ju-Hyun Kim et al., "Effect of additives on the crystallization and the permeation of ketoprofen from adhesive matrix", International Journal of Pharmaceutics, Apr. 2, 2002, vol. 236, Issues 1-2, pp. 81-85 (3 pages total) [Abstract].
Yasser Shahzad et al., "Development of solid dispersions of artemisinin for transdermal delivery", International Journal of Pharmaceutics, 2013, vol. 457, pp. 197-205 (9 pages total).

\* cited by examiner

| | Optical image | Polarization image |
|---|---|---|
| Comparative Example 1 | | |
| Comparative Example 2 | | |
| Comparative Example 3 | | |

| | Optical image | Polarization image |
|---|---|---|
| Example 4 | | |
| Example 5 | | |
| Example 6 | | |
| Example 7 | | |

[Figure 3]

| | Optical image | Polarization image |
|---|---|---|
| Example 2 |  |  |
| Example 4 |  |  |

PHARMACEUTICAL COMPOSITION CONTAINING (R)-N-[1-(3,5-DIFLUORO-4-METHANE-SULFONYLAMINO-PHENYL)-ETHYL]-3-(2-PROPYL-6-TRIFLUOROMETHYLPYRIDIN-3-YL)-ACRYLAMIDE AND METHOD FOR INHIBITING CRYSTAL FORMATION THEREOF

CROSS REFERENCE TO RELATED APPLICATIONS

This application is a National Stage of International Application No. PCT/KR2019/003297, filed Mar. 21, 2019, claiming priority to Korean Patent Application No. 10-2018-0044818, filed Apr. 18, 2018.

TECHNICAL FIELD

The present application claims the benefit of priority based on Korean Patent Application No. 10-2018-0044818 filed on Apr. 18, 2017, the entire contents of which are incorporated herein by reference.

One aspect of the present disclosure relates to a pharmaceutical composition comprising (R)-N-[1-(3,5-difluoro-4-methanesulfonylamino-phenyl)-ethyl]-3-(2-propyl-6-trifluoromethyl-pyridin-3-yl)-acrylamide having excellent feeling of use and a method for suppressing the formation of crystals thereof.

BACKGROUND ART

The compound (R)-N-[1-(3,5-difluoro-4-methanesulfonylamino-phenyl)-ethyl]-3-(2-propyl-6-trifluoromethyl-pyridin-3-yl)-acrylamide is represented by Formula 1 below, and is a compound disclosed in Example 230 of International Patent Publication WO 2008/013414:

<Formula 1>

The compound of Formula 1 is a very useful compound that has a vanilloid receptor antagonistic activity and is expected to be used as an effective therapeutic agent for skin diseases such as pain, neuropathy, and atopic dermatitis, and inflammatory diseases. In particular, it may be desirable to apply topically directly to the skin in case of muscle pain or skin disease. Therefore, an external preparation is required as one of the formulation forms suitable for the compound of Formula 1.

Thus, during repeated studies of one aspect of the present disclosure, the inventors of one aspect of the present disclosure found that in the experiment of solubility for the compound of Formula 1, the solubility in water is less than 0.1 mg/mL, which is poorly soluble. In order to formulate a drug, which is poorly soluble in water, into an external preparation, water is usually not used, or its content is minimized, and a solvent capable of solubilizing a poorly soluble material is used. However, this method may adversely affect the skin or worsen the feeling of use. In particular, when applied to a patient with increased sensitivity due to a disease such as atopic dermatitis, atopic dermatitis may be worsened or medication compliance may be lowered, which may ultimately affect the therapeutic effect. In addition, it was found that the compound of Formula 1 is not only poorly soluble in water, but also significantly lower in solubility in oil.

In order to improve the poorly soluble property in water, an attempt was made to form an external preparation after making the poorly soluble material into an amorphous state using a polymer. However, the amorphous state is basically unstable and is particularly vulnerable to temperature and moisture. Therefore, the external preparation usually contains water in itself, so it is difficult to suppress the crystallization of the amorphous form by a conventional method.

Another conventional technique for external preparations containing poorly soluble substances is to mix separately prepared solid dispersions into the solvent preparation of the external preparations. However, this technique did not provide specific data that the finished product of external preparation inhibits crystallization to the extent that it is possible to secure the shelf life of the drug.

Another conventional technique for external preparations containing poorly soluble substances is to mix separately prepared solid dispersions into the solvent preparation of the external preparations. However, this technique did not provide specific data that the finished product of external preparation inhibits crystallization to the extent that it is possible to secure the shelf life of the drug (J. DRUG DEL. SCI. TECH., 21 (6) 509-516 2011, Int J App Pharm.).

As such, it is necessary to develop a pharmaceutical composition that contains the compound of Formula 1, a compound poorly soluble in water and oil, which is medicinally effective but not easy to formulate, and that has excellent feeling of use and suppresses the formation of crystals for at least two years of use.

DISCLOSURE

Technical Problem

As a result of conducting research in various ways to solve the above problems, the inventors of one aspect of the present disclosure have confirmed that by using a vinylpyrrolidone-based polymer, a pharmaceutical composition is prepared, which has the property that the formation of crystals is delayed for a long time, and has excellent feeling of use, thereby having completed one aspect of the present disclosure.

Therefore, it is an object of one aspect of the present disclosure to provide a pharmaceutical composition which contains (R)-N-[1-(3,5-difluoro-4-methanesulfonylamino-phenyl)-ethyl]-3-(2-propyl-6-trifluoromethyl-pyridin-3-yl)-acrylamide, has the property that the formation of crystals is suppressed, and has excellent feeling of use.

Technical Solution

In order to achieve the above objects, one aspect of the present disclosure provides a pharmaceutical composition comprising the compound of (R)-N-[1-(3,5-difluoro-4-methanesulfonylamino-phenyl)-ethyl]-3-(2-propyl-6-trifluoromethyl-pyridin-3-yl)-acrylamide represented by the following Formula 1 as a first component, and vinylpyrrolidone-based polymer as a second component.

In addition, another aspect of the present disclosure provides a method for suppressing the formation of crystals from a pharmaceutical composition comprising the compound of (R)-N-[1-(3,5-difluoro-4-methanesulfonylaminophenyl)-ethyl]-3-(2-propyl-6-trifluoromethyl-pyridin-3-yl)-acrylamide represented by Formula 1 as a first component, which comprises the step of adding a vinylpyrrolidone-based polymer as a second component.

Advantageous Effects

The pharmaceutical composition of one aspect of the present disclosure suppresses the crystallization of compound of Formula 1 which is an active component.

BEST MODE

Hereinafter, the present invention will be described in more detail to assist in understanding the present invention.

The terms and words used in the present specification and claims should not be construed as limited to ordinary or dictionary terms, and should be construed in a sense and concept consistent with the technical idea of the present invention, based on the principle that the inventor can properly define the concept of a term to describe his invention in the best way possible.

One aspect of the present disclosure provides a pharmaceutical composition in which the formation of crystals is suppressed for a long time by using a specific polymer.

The pharmaceutical composition according to one aspect of the present disclosure comprises the compound represented by the following Formula 1 as a first component, and a vinylpyrrolidone-based polymer as a second component:

<Formula 1>

The compound represented by Formula 1 is an antagonist of vanilloid receptor-1 (VR1, or TRPV1 (transient receptor potential vanilloid-1)), which is useful for skin diseases such as pain, neuropathy, and atopic dermatitis, and inflammatory diseases, etc. The compound of Formula 1 of one aspect of the present disclosure, its preparation method, and vanilloid receptor antagonistic activity are disclosed in detail in International Publication WO 2008/013414, and all contents disclosed in this document are incorporated herein by reference.

In one aspect of the present disclosure, the compound of Formula 1 comprises both the parent compound and pharmaceutically acceptable salts. Examples of such salts are (1) acid addition salts formed with inorganic acids or with organic acids; or (2) salts formed when acidic protons present in the parent compound are substituted.

The compound of Formula 1, which is the first component of the pharmaceutical composition according to one aspect of the present disclosure, may be contained in an amount of 0.1 to 1.5% by weight. Specifically, the content of the first component is 0.1% by weight or more, 0.5% by weight or more, or 0.8% by weight or more, and 1.2% by weight or less, or 1.5% by weight or less. If the content of the compound represented by Formula 1 is less than 0.1% by weight, the desired therapeutic effect may not appear. If the content of the compound is more than 1.5% by weight, the content of the solvent and the second component, vinylpyrrolidone-based polymer, may be relatively reduced, so that the feeling of use can be lowered and the effect of suppressing the formation of crystals can be reduced.

The solvents used according to one aspect of the present disclosure can be used to dissolve the poorly soluble compound of Formula 1. As such solvents, solvents which have a high solubility with respect to the solvent of compound of Formula 1 and thus is capable of dissolving compound of Formula 1 in small amounts and have high safety are suitable.

The solvent used according to one aspect of the present disclosure may be a solvent having a solubility for compound of Formula 1 of 100 mg/mL or more, 120 mg/mL or more, or 150 mg/mL or more.

The solvent used according to one aspect of the present disclosure may be one or more selected from the group consisting of diethylene glycol monoethylether, polyethylene glycol, 2-pyrrolidone, and dimethyl sulfoxide, or one or more selected from the group consisting of diethylene glycol monoethylether and polyethylene glycol, or polyethylene glycol. As a solvent used according to one aspect of the present disclosure, the polyethylene glycol may be polyethylene glycol 300 or polyethylene glycol 400, and polyethylene glycol 400 may be used.

The solvent may be contained in an amount of 5 to 20% by weight. Specifically, the content of the solvent is 5% by weight or more, or 8% by weight or more, and 12% by weight or less, 15% by weight or less, or 20% by weight or less. If the content of the solvent is less than 5% by weight, the compound represented by Formula 1 cannot be completely dissolved. If the content of the solvent is more than 20% by weight, the feeling of use may be deteriorated because the solvent is excessively contained.

The vinylpyrrolidone-based polymer used in one aspect of the present disclosure suppresses the formation of crystals from the compound of Formula 1, which is the active component of the pharmaceutical composition of one aspect of the present disclosure, for a long time, and promotes the feeling of use. The vinylpyrrolidone-based polymer is easy to obtain and has a property that is easy to change the structure through a chemical reaction, and is generally widely used as an excipient in pharmaceutical compositions, but in one aspect of the present disclosure, it can be used to suppress the formation of crystals of compound of Formula 1.

The vinylpyrrolidone-based polymer used in one aspect of the present disclosure is at least one selected from the group consisting of polyvinyl pyrrolidone, copovidone, a vinylpyrrolidone/dimethylaminoethyl methacrylate copolymer, a vinylcaprolactam/vinylpyrrolidone/dimethylaminoethylmethacrylate copolymer, an alkylated vinylpyrrolidone polymer and a vinylpyrrolidone/styrene copolymer, or is polyvinyl pyrrolidone or copovidone.

The content of the vinylpyrrolidone-based polymer may be 1 to 5% by weight. Specifically, the content of the vinylpyrrolidone-based polymer is 1% by weight or more, and 3% by weight or less, or 5% by weight or less, or is 2.5% by weight. If the content of the vinylpyrrolidone-based polymer is less than 1% by weight, the suppression effect of the formation of crystals is insignificant, and crystals are precipitated from the pharmaceutical composition. If the content of the vinylpyrrolidone-based polymer exceeds 5% by weight, crystals are not precipitated, but the feeling of use may be deteriorated.

In addition, the vinylpyrrolidone-based polymer may be contained in a weight ratio of 1 to 3:1, or 1.5 to 3:1, or 2 to 3:1 to the compound represented by Formula 1. If the weight ratio is less than the weight ratio, the suppression effect of the formation of crystals is insignificant, and crystals can be precipitated from the pharmaceutical composition.

In addition, the vinylpyrrolidone-based polymer may have a K-value of 10 to 100. Specifically, the K-value is 10 or more, 20 or more, or 25 or more, and 35 or less, 50 or less, or 100 or less. The K-value represents the viscosity index related to molecular weight, and is calculated by the equation of Fikentscher (K=$(1.5 \log \eta_{rel} -1)/(0.15+0.003c)+ (300c \log \eta_{rel}+(c+1.5c\log \eta_{rel})^2)^{1/2}/(0.15c+0.003c^2)$ along with the relative viscosity measured by a capillary viscometer at 25° C. In one aspect of the present disclosure, if the K-value of vinylpyrrolidone-based polymer is less than 10, the suppression effect of the formation of crystals is insignificant, and crystals can be precipitated from the pharmaceutical composition. If the K-value exceeds 100, since the feeling of use may not be good, in particular, when applied to patients with increased sensitivity, such as atopic dermatitis, atopic dermatitis may be worsened or medication compliance may be lowered, which may ultimately affect the therapeutic effect.

In one aspect of the present disclosure, the vinylpyrrolidone-based polymer suppresses the formation of crystals to the extent that crystals of compound of Formula 1 are not observed by a microscope (for example, BX50 manufactured by Olympus) at a magnification of 100 times or more, specifically at a magnification of 100 times, or at a magnification of 500 times, or at a magnification of 1000 times. At this time, whether or not crystals were precipitated was judged to have precipitated when irregular particles of dark color are observed in the optical image, and at the same time, anisotropic particles are observed in the polarization image at the same position.

The pharmaceutical composition of one aspect of the present disclosure may be formulated into an external preparation of skin, and may be formulated into a cream, a gel, a patch, a spraying agent, an ointment, a plaster, a lotion, a liniment, a cataplasma, an essence, a pack, a powder, an oil, a wax, a spray, a paste, a solution, a suspension, an emulsion, or a soap.

On the other hand, depending on the desired formulation, it may further comprise any known ingredients commonly used in the art to the extent that the effect of the compound of Formula 1 is not impaired. According to one embodiment, it may further comprise additives selected from the group consisting of carriers, emulsifiers, moisturizers, skin conditioning agents, surfactants, chelating agents, antioxidants, fungicides, stabilizers, and any combinations thereof.

The carrier may be, but is not limited to, animal fibers, vegetable fibers, waxes, paraffin, starch, tragacanth, cellulose derivatives, polyethylene glycol, silicone, bentonite, silica, talc, zinc oxide, lactose, aluminum hydroxide, calcium silicate, polyamide powder, water, ethanol, isopropanol, ethyl carbonate, ethyl acetate, benzyl alcohol, benzyl benzoate, propylene glycol, 1,3-butyl glycol, oils, glycerol aliphatic ester, liquid diluent, ethoxylated isostearyl alcohol, or suspension agents such as polyoxyethylen sorbitol ester and polyoxyethylen sorbitan ester, or microcrystalline celluloses, aluminum metahydroxide, agar, aliphatic alcohol sulfate, aliphatic alcohol ether sulfate, sulfosuccinic acid monoester, isethionate, imidazolinium derivatives, methyltaurate, sarcosinate, fatty acid amide ether sulfate, alkylamidobetaine, aliphatic alcohols, fatty acid glycerides, fatty acid diethanolamides, vegetable oils, linoline derivatives, or ethoxylated glycerol fatty acid esters, etc.

The moisturizer may be, but is not limited to, glycerin, glyceryl stearate, and the like.

The skin conditioning agent may be, but is not limited to, cyclomethicone, dimethicone and the like.

The surfactant may be, but is not limited to, polyoxyethylene-sorbitan-fatty acid esters, polyoxyethylene fatty acid esters, sorbitan fatty acid esters, a polyoxyethylene-polyoxypropylene copolymer, cetearyl glucoside, mono/diglycerides and the like.

The chelating agent may be, but is not limited to, ethylenediaminetetraacetic acid sodium (EDTA), α-hydroxy fatty acid, lactoferrin, α-hydroxy acid, citric acid, lactic acid, malic acid, bilirubin, biliverdin, and the like.

The antioxidant may be, but is not limited to, butylhydroxyanisole, dibutylhydroxytoluene or propyl gallate and the like.

In addition, ingredients that can be blended into the pharmaceutical composition may be a pH adjusting agent, a plasticizer, a solubilizer, a gelling agent, a binder, an isotonic agent, a pain reliever, a preservative, a dispersant, an opacifier, an antioxidant, an osmotic agent, an antifoaming agent, a wetting agent, a thickener, an adhesive, a masking reagent, a colorant, a flavoring agent, a film former, a suspending agent, a volatilization inhibitor, an adsorbent, a fat and an oil, an emollient, an organic pigment and an inorganic pigment, an organic powder, an ultraviolet absorber, an alcohol, a blood circulation accelerator, a cold-sensation agent, an adiaphoretic, and the like.

The single dose of the pharmaceutical composition of one aspect of the present disclosure depends on the patient's condition, weight, and severity of the disease, the type of composition, and the route and duration of administration. However, as the application amount when applied by external preparation of skin, the amount (1 finger-tip unit (FTU), 0.5 g) when the cream is squeezed in a row up to the length of the last node of the patient's index finger corresponds to the appropriate amount of one application to be applied to an area twice the size of the palm of the patient (~2% BSA (Body Surface Area)).

At this time, BSA (Body Surface Area) refers to a lesion area, and is a value obtained by evaluating the area of the lesion area out of 100% of the total area of the skin according to the Rule of 9.

Specifically, when the subject to which the pharmaceutical composition of one aspect of the present disclosure is administered is an atopic dermatitis patient, for example, a patient with a lesion of 5% to 30% BSA, the single dose may be 25 mg to 150 mg, and may be appropriately adjusted in consideration of the size and shape of the lesion, the severity of symptom, and age within the range of the single dose.

Since the pharmaceutical composition of one aspect of the present disclosure as described above contains the compound of Formula 1, a TRPV1 antagonist, as an active component, it can be used for the treatment of diseases that can be treated with the TRPV1 antagonistic effect, for example, skin diseases such as pain and atopic dermatitis. In addition, since feeling of use is also enhanced, it can be specially formulated into an external preparation of skin.

The pharmaceutical composition of one aspect of the present disclosure may be in the form of an oil-in-water (O/W) emulsion comprising at least one component selected from the group consisting of, (1) a compound of Formula 1, which is a first component, as a drug;

(2) a vinylpyrrolidone-based polymer as a second component;

(3) at least one component selected from the group consisting of diethylene glycol monoethylether, polyethylene glycol, 2-pyrrolidone, and dimethyl sulfoxide as a solvent;

(4) water as a component of the aqueous phase;

(5) at least one component selected from the group consisting of PEG-30 hydrogenated castor oil, medium chain triglycerides, cetostearyl alcohol, squalane, and cyclomethicone as an oil phase component;

(6) at least one component selected from the group consisting of polyoxyethylene-sorbitan-fatty acid esters, polyoxyethylene fatty acid esters, sorbitan fatty acid esters, a polyoxyethylene-polyoxypropylene copolymer, cetearyl glucoside, and mono/diglycerides as a surfactant;

(7) at least one component selected from the group consisting of xanthan gum, gelatin, gellan gum, carrageenan, and carbomer as a thickener.

The content of the compound of Formula 1, which is the first component in the composition of one aspect of the present disclosure as a drug, may be 0.1 to 1.5% by weight based on the total weight of the composition. The content of the vinylpyrrolidone-based polymer which is the second component, may be 1 to 5% by weight based on the total weight of the composition. The content of the solvent may be to 20% by weight based on the total weight of the composition. The content of the aqueous phase may be 45 to 90% by weight based on the total weight of the composition. The content of the oil phase may be 5 to 30% by weight. The content of the surfactant may be 1 to 10% by weight. The content of the thickener may be 0.01 to 5% by weight.

In addition, another aspect of the present disclosure provides a method for suppressing the formation of crystals from a pharmaceutical composition comprising the compound of (R)-N-[1-(3,5-difluoro-4-methanesulfonylamino-phenyl)-ethyl]-3-(2-propyl-6-trifluoromethyl-pyridin-3-yl)-acrylamide represented by Formula 1 as a first component, and further comprises a step of adding a vinylpyrrolidone-based polymer as a second component.

Item 1. A pharmaceutical composition comprising the compound of (R)-N-[1-(3,5-difluoro-4-methanesulfonylamino-phenyl)-ethyl]-3-(2-propyl-6-trifluoromethyl-pyridin-3-yl)-acrylamide represented by the following Formula 1 and a vinylpyrrolidone-based polymer:

<Formula 1>

Item 2. The pharmaceutical composition according to Item 1, wherein the vinylpyrrolidone-based polymer suppresses the formation of crystals of the compound of Formula 1.

Item 3. The pharmaceutical composition according to Item 1 or 2, wherein crystals of the compound of Formula 1 are not observed from the pharmaceutical composition, when observing by an optical microscope at a magnification of 100 times or more, at a magnification of 500 times or more, or at a magnification of 1000 times or more.

Item 4. The pharmaceutical composition according to Item 3, wherein the optical microscope is equipped with a polarization filter.

Item 5. The pharmaceutical composition according to any one of Items 1 to 4, wherein the vinylpyrrolidone-based polymer comprises any one or more of the following (i) to (iii):

(i) its K-value is 10 to 100, 20 to 50, or 25 to 35, (ii) its content is 1 to 5% by weight, 1 to 3% by weight, or 2.5% by weight based on the total weight of the composition, or (iii) its weight ratio to the compound represented by Formula 1 is 1 to 3:1, 1.5 to 3:1, or 2 to 3:1.

Item 6. The pharmaceutical composition according to any one of Items 1 to 5, wherein the vinylpyrrolidone-based polymer is at least one selected from the group consisting of polyvinyl pyrrolidone, copovidone, a vinylpyrrolidone/dimethylaminoethyl methacrylate copolymer, a vinylcaprolactam/vinylpyrrolidone/dimethylaminoethyl methacrylate copolymer, an alkylated vinylpyrrolidone polymer and a vinylpyrrolidone/styrene copolymer, or is polyvinyl pyrrolidone or copovidone.

Item 7. The pharmaceutical composition according to any one of Items 1 to 6, further comprising a solvent having a solubility for the compound of Formula 1 of 100 mg/mL or more, 120 mg/mL or more, or 150 mg/mL or more.

Item 8. The pharmaceutical composition according to Item 7, wherein the solvent is at least one selected from the group consisting of diethylene glycol monoethylether, polyethylene glycol, 2-pyrrolidone, and dimethyl sulfoxide, at least one selected from the group consisting of diethylene glycol monoethylether, dimethyl sulfoxide and polyethylene glycol, or polyethylene glycol.

Item 9. The pharmaceutical composition according to Item 7, wherein the polyethylene glycol is polyethylene glycol 300 or polyethylene glycol 400, or polyethylene glycol 400

Item 10. The pharmaceutical composition according to any one of Items 7 to 9, wherein the solvent is contained in an amount of 5 to 20% by weight, 5 to 15% by weight, 8 to 12% by weight, or 10% by weight, based on the total weight of the composition.

Item 11. The pharmaceutical composition according to any one of Items 1 to 10, wherein the compound represented by Formula 1 is contained in an amount of 0.1 to 1.5% by weight, 0.5 to 1.2% by weight, or 0.8 to 1.2% by weight.

Item 12. The pharmaceutical composition according to any one of Items 1 to 11, wherein the pharmaceutical composition is formulated into an external preparation applied to the skin.

Item 13. The pharmaceutical composition according to any one of Items 1 to 12, wherein the pharmaceutical composition is formulated into a cream, a gel, a patch, a spraying agent, an ointment, a plaster, a lotion, a liniment, a paste, or a cataplasma formulation.

Item 14. A method for suppressing the formation of crystals of the compound of the following Formula 1 from a pharmaceutical composition comprising the compound of (R)-N-[1-(3,5-difluoro-4-methanesulfonylamino-phenyl)-ethyl]-3-(2-propyl-6-trifluoromethyl-pyridin-3-yl)-acrylamide represented by the following Formula 1, which comprises a step of adding polyvinyl pyrrolidone or copovidone:

<Formula 1>

In the following experimental examples, the compound of Formula 1 is (R)-N-[1-(3,5-difluoro-4-methanesulfonylamino-phenyl)-ethyl]-3-(2-propyl-6-trifluoromethyl-pyridin-3-yl)-acrylamide.

Preliminary Experimental Example 1: Selection of Suitable Solvent for Compound of Formula 1

In order to select a solvent capable of solubilizing the compound of Formula 1, which is poorly soluble in oil as well as water, experiments on the solubility of compound of Formula 1 were performed on various solvents listed in Table below. Since solvent that gives high solubility can dissolve the compound of Formula 1 in a small amount compared to a solvent that gives low solubility, in particular, when formulated into an external preparation of skin, a relatively higher amount of water may be contained, so that the feeling of use can be further enhanced.

An excessive amount of the compound of Formula 1 was added to 1 mL of each solvent shown in Table 1 below, and stirred at 25° C. at 200 rpm for 24 hours while shaking (Shaking incubator, SI 600R, JEIO TECH, Korea). Thereafter, centrifugation was performed at 10,000 rpm for 10 minutes, and the supernatant was filtered using a membrane filter (0.2 μm), diluted appropriately with methanol, and analyzed by HPLC. From the results of the analysis, solubility in each solvent of compound of Formula 1 was calculated, and the results are shown in Table 1 below.

TABLE 1

| Chemical name | Solubility(mg/mL) |
|---|---|
| Purified water | 0.05 |
| Diethylene glycol monoethyl ether | 288.92 |
| Acetonitrile | 108.06 |
| Methanol | 177.68 |

TABLE 1-continued

| Chemical name | Solubility(mg/mL) |
|---|---|
| Ethanol | 75.32 |
| Dimethyl sulfoxide | 631.85 |
| Polyethylene glycol (PEG) 400 | 167.73 |
| Miglyol | 1.40 |
| Ethyl oleate | 1.00 |
| Corn oil | 1.80 |
| Dimethylacetamide | 80.00 |
| Propylene glycol | 25.00 |
| Polysorbate 80 | 11.80 |
| Caprylocaproyl polyoxyl-8 glycerides | 46.70 |
| Lauroyl macrogol-32 glycerides | 24.10 |
| Polyethylene glycol-35 castor oil | 2.70 |
| 2-Pyrrolidinone | 212.00 |
| Polyoxyl 40 hydrogenated castor oil | 36.00 |
| Polysorbate 20 | 47.97 |
| Polysorbate 60 | 35.04 |
| Polysorbate 40 | 37.02 |
| Propylene glycol monocaprylate | 75.00 |
| Octyldodecanol | 1.77 |
| Oleyl Alcohol | 6.32 |
| Isopropyl myristate | 1.18 |
| Oleic acid | 0.43 |
| Cocoyl caprylocaprate | 0.46 |
| Propylene glycol monolaurate | 7.75 |
| Oleoyl polyoxyl-6 glycerides | 4.36 |
| Glycerol | 0.84 |
| Polyethylene glycol (PEG) 300 | 145.73 |
| Poloxamer 124 | 66.69 |
| Triglycerides, Medium chain | 1.9 |
| Triacetin | 56.53 |

As can be seen from Table 1, the compound of Formula 1 shows high solubility of 100 mg/ml or more with respect to Dimethyl sulfoxide (DMSO, Sigma-Aldrich), diethylene glycol monoethylether (Sigma-Aldrich), 2-pyrrolidone (Aldrich), and polyethylene glycol (PEG, Sanyo), so they can be used as a solvent suitable for the compound of Formula 1. However, it is difficult to formulate simply by using these solvents, because the solubility of the compound of Formula 1 is significantly reduced in a composition having a high aqueous phase content. For example, the solubility in aqueous PEG 400 10% (w/w) solution is about 0.08 mg/mL and is almost insoluble (practically insoluble).

Preparation Example 1: Preparation of Compositions of Reference Examples of the Embodiment of the Invention 1) Preparation of Vinylpyrrolidone-Based Polymer Four vinylpyrrolidone-based polymers having properties as described in Table 2 below, namely three polyvinyl pyrrolidones (Kollidon 17, Kollidon 30, and Kollidon 90, BASF) and one copovidone (Kollidon VA 64, BASF)) were prepared.

TABLE 2

| | vinylpyrrolidone-based polymer | k-vlaue |
|---|---|---|
| Reference Example 1 | Kollidon 17 | 15.3-18.0 |
| Reference Example 2 | Kollidon 30 | 27.0-32.1 |

TABLE 2-continued

|  | vinylpyrrolidone-based polymer | k-vlaue |
|---|---|---|
| Reference Example 3 | Kollidon 90 | 81.0-96.3 |
| Reference Example 4 | Kollidon VA 64 | 25.2-30.8 |

2) Preparation of Compositions of Reference Examples 1 to 4 of the Embodiment of the Invention A first solution was prepared by dissolving 1 g of compound of Formula 1 in 10 g of PEG400 which is one of the solvents confirmed to be suitable in Preliminary Experimental Example 1. A second solution was prepared by dissolving 2 g of each of Kollidon 17, Kollidon 30, and Kollidon 90 and Kollidon VA 64 shown in Table 2 in 87 g of purified water. The compositions of Reference Examples 1 to 4 of the embodiment of the invention were prepared by adding the first solution to the second solution.

Preparation Example 2: Preparation of Cream for External Preparation of Skin

Creams for the external preparation of skin was prepared by using the components for a conventional cream formulation, the compound of Formula 1 as the first component, the second component (vinylpyrrolidone-based polymer), and solvent (diethylene glycol monoethylether, polyethylene glycol, dimethyl sulfoxide), as shown in Table 3 below.

The oil phase and aqueous phase shown in Table 3 are prepared by heating each of them, the compound of Formula 1 was prepared by dissolving it in a solvent, and a thickener was prepared by pre-dispersing it, and each vinylpyrrolidone-based polymer was prepared by dissolving it in water.

After that, the oil phase and aqueous phase are first emulsified at 65° C., and then vinylpyrrolidone-based polymer dissolved in water is added and homogenized. Subsequently, the compound of Formula 1 dissolved in solvent was added, and the thickener and the additives were added, homogenized, and then cooled to 35° C. to prepare a pharmaceutical composition for an external preparation of skin as a cream formulation.

TABLE 3

| Unit: wt. % | Component | Comparative Example 1 | Comparative Example 2 | Comparative Example 3 | Example 1 | Example 2 | Example 3 | Example 4 | Example 5 | Example 6 | Example 7 |
|---|---|---|---|---|---|---|---|---|---|---|---|
| Oil phase | PEG-30 hydrogenated castor oil | 3 | 3 | 3 | 3 | 3 | 3 | 3 | 3 | 3 | 3 |
|  | Medium chain triglyceride | 0 | 0 | 0 | 0 | 0 | 0 | 0 | 0 | 0 | 0 |
|  | Cetostearyl alcohol | 0 | 0 | 0 | 0 | 0 | 0 | 0 | 0 | 0 | 0 |
|  | Squalane | 3 | 3 | 3 | 3 | 3 | 3 | 3 | 3 | 3 | 3 |
|  | Cyclomethicone | 0 | 0 | 0 | 0 | 00 | 0 | 0 | 0 | 0 | 0 |
| Surfactant | Sorbitan stearate | 0.4 | 0.4 | 0.4 | 0.4 | 0.4 | 0.4 | 0.4 | 0.4 | 0.4 | 0.4 |
|  | Polysorbate 60 | 0 | 0 | 0 | 0 | 0 | 0 | 0 | 0 | 0 | 0 |
|  | Cetearyl glucoside | 1.5 | 1.5 | 1.5 | 1.5 | 1.5 | 1.5 | 1.5 | 1.5 | 1.5 | 1.5 |
|  | Mono/diglycerides | 0 | 0 | 0 | 0 | 0 | 0 | 0 | 0 | 0 | 0 |
| Thickener | Carbomer | 0.2 | 0.2 | 0.2 | 0.2 | 0.2 | 0.2 | 0.2 | 0.2 | 0.2 | 0.2 |
| Neutralizing agent | KOH | 0.1 | 0.1 | 0.1 | 0.1 | 0.1 | 0.1 | 0.1 | 0.1 | 0.1 | 0.1 |
| First component | Compound of Formula 1 | 0 | 0 | 1 | 1 | 1 | 1 | 1 | 1 | 1 | 1 |
| Aqueous phase | Butylene glycol | 3 | 3 | 3 | 3 | 3 | 3 | 3 | 3 | 3 | 3 |
|  | Glycerin | 5 | 5 | 5 | 5 | 5 | 5 | 5 | 5 | 5 | 5 |
|  | Propylene glycol | 0 | 0 | 0 | 0 | 0 | 0 | 0 | 0 | 0 | 0 |
|  | Purified water | remainder | remainder | remainder | remainder | remainder | remainder | remainder | remainder | remainder | remainder |
| Solvent | Polyethylene glycol 300 | 0 | 0 | 0 | 0 | 0 | 0 | 0 | 0 | 10 | 0 |
|  | Polyethylene glycol 400 | 10 | 10 | 10 | 10 | 10 | 10 | 10 | 0 | 0 | 0 |
|  | Diethylene glycol monoethyl ether | 0 | 0 | 0 | 0 | 0 | 0 | 0 | 10 | 0 | 0 |
|  | DMSO | 0 | 0 | 0 | 0 | 0 | 0 | 0 | 0 | 0 | 10 |
| Second component | Kollidon 17 | 0 | 2 | 0 | 2 | 0 | 0 | 0 | 0 | 0 | 0 |
|  | Kollidon 30 | 0 | 0 | 0 | 0 | 2 | 0 | 0 | 0 | 0 | 0 |
|  | Kollidon 90 | 0 | 0 | 0 | 0 | 0 | 2 | 0 | 0 | 0 | 0 |
|  | Kollidon VA 64 | 0 | 0 | 0 | 0 | 0 | 0 | 2 | 2 | 2 | 2 |
| Additives | Preservative, colorant, flavoring agent | q.s. | q.s. | q.s. | q.s. | q.s. | q.s. | q.s. | q.s. | q.s. | q.s. |

In addition to the cream formulation, the following formulations may also be prepared as formulations containing the compound of Formula 1 and suppressing the formation of crystals.

Formulation Example 1

Gel

A gel containing the compound of Formula 1, a solvent (PEG 400), and a vinylpyrrolidone-based polymer (Kollidon 30) of the embodiment of the invention was prepared by a conventional method according to the composition shown in Table 4 below.

TABLE 4

| Component | wt. % |
|---|---|
| Compound of Formula (1) | 1 |
| Solvent (PEG 400) | 10 |
| Vinylpyrrolidone-based polymer (Kollidon 30) | 2 |
| Alpha-ketoglutaric acid | 1.0 |
| Niacinamide | 1.0 |
| Beta-1,3-glucan | 0.1 |
| Ethylenediamine sodium acetate | 0.05 |
| Glycerine | 5.0 |
| Carboxyvinyl polymer | 0.3 |
| Ethanol | 5.0 |
| Triethanolamine | 0.3 |
| Preservative, flavoring agent | 0.1 |
| Purified water | remainder |

Formulation Example 2

Ointment

An ointment containing the compound of Formula 1, a solvent (PEG 400), and a vinylpyrrolidone-based polymer (Kollidon 30) of the embodiment of the invention by a conventional method according to the composition shown in Table 5 was prepared.

TABLE 5

| Component | wt. % |
|---|---|
| Compound of Formula (1) | 1 |
| Solvent (PEG 400) | 10 |
| Vinylpyrrolidone-based polymer (Kollidon 30) | 2.5 |
| Alpha-ketoglutaric acid | 1.0 |
| Niacinamide | 1.0 |
| Beta-1,3-glucan | 10.0 |
| Beewax | 10.0 |
| Polysorbate | 5.0 |
| PEG 60 hardened castor oil | 2.0 |
| Sorbitan sesquioleate | 0.5 |
| Vaseline | 5.0 |
| Liquid paraffin | 10.0 |
| Squalane | 5.0 |
| Shea butter | 3.0 |
| Caprylic/capric triglyceride | 5.0 |
| Glycerine | 10.0 |
| Propylene glycol | 10.2 |
| Triethanolamine | 0.2 |
| Preservative, flavoring agent | 0.1 |
| Purified water | remainder |

Formulation Example 3

Lotion

A lotion containing the compound of Formula 1, a solvent (PEG 400), and a vinylpyrrolidone-based polymer (Kollidon 30) of the embodiment of the invention was prepared by a conventional method according to the composition shown in Table 6 below.

TABLE 6

| Component | wt. % |
|---|---|
| Compound of Formula (1) | 1 |
| Solvent (PEG 400) | 10 |
| Vinylpyrrolidone-based polymer (Kollidon 30) | 2 |
| Biovaderm (Biova inc.) Hydrolyzed egg shell | 10.0 |
| Shea butter | 3.0 |
| Caprylic/capric triglyceride | 5.0 |
| Glycerine | 10.0 |
| Propylene glycol | 10.2 |
| Triethanolamine | 0.2 |
| Preservative, flavoring agent | 0.1 |
| Purified water | remainder |

Experimental Example 1: Particle Size and Dispersion Stability of the Composition of Preparation Example 1

The particle size and dispersion stability of the compositions of Reference Examples 1 to 4 of the embodiment of the invention prepared in the above preparation examples were measured.

The particle size was measured by dynamic light scattering using a laser particle size analyzer (Zetasizer Nano ZS, Malvern Instruments, Southborough, UK). In addition, dispersion stability was measured for 24 hours every 2 hours at a temperature of 50° C. using a measuring device (Turbiscan AGS, Formulaction, Toulouse, France) to calculate the Turbiscan Stability Index (TSI). As described above, the measured particle size (unit: nm) and TSI are described in Table 7 below.

Turbiscan, which is an analysis technique for dispersion stability used in the embodiment of the invention, is a technique for optically measuring the dispersion of a formulation using multiple light scattering and can analyze all the phenomenon in which dispersion stability decreases, that is, a phenomenon of particle migration such as sedimentation and creaming, and the phenomenon of particle size variation such as flocculation and coalescence and thus is used for various stability studies (Talanta, Volume 50, Issue 2, 13 September 1999, Langmuir, 2004, 20, 9007-9013, Med Chem. 2015 June; 11(4): 391-399.). Also, it means that the larger the particle size, the more crystals grow. Therefore, the dispersion stability of the pharmaceutical composition can be predicted through the measurement of TSI and size measured in the embodiment of the invention, from which the crystallization process of the active compound can be deduced.

TABLE 7

| | Vinylpyrrolidone-based polymer | Size(nm) | TSI |
|---|---|---|---|
| Reference Example 1 | Kollidon 17 | 1695.3 ± 929.0 | 9.6 ± 2.5 |
| Reference Example 2 | Kollidon 30 | 789.6 ± 36.8 | 7.6 ± 0.4 |
| Reference Example 3 | Kollidon 90 | 4205.3 ± 191.2 | 18.7 ± 1.9 |
| Reference Example 4 | Kollidon VA 64 | 685.5 ± 26.1 | 6.8 ± 0.5 |

As can be seen from Table 7 above, it was confirmed that Reference Examples 2 and 4 of the embodiment of the invention have crystals having a relatively small particle size, and the TSI is also relatively low, on average from 6 to 8. From this, it could be expected that the formation of crystals of the compound of Formula 1, which is an active component, is significantly suppressed in the composition of the embodiment of the invention using Kollidon 30 or Kollidon VA 64.

Referring to Table 7, the tendency of TSI was not observed in the whole vinylpyrrolidone-based polymer, from which it can be seen that there is a difference in terms of interaction between the compound of Formula 1 and each vinylpyrrolidone-based polymer.

In addition, it was confirmed that even if the same vinylpyrrolidone-based polymer is used, when the k-vlaue of the vinylpyrrolidone-based polymer has a value of about 25 to 35, there is a tendency that the size and TSI of the active material crystal in the composition become small.

As described above, it can be expected that the vinylpyrrolidone-based polymers in Reference Examples 1 to 4 all will show the effect of suppressing the formation of crystals of the compound of Formula 1, which is the active component of the pharmaceutical composition of the embodiment of the invention, and in particular, Kollidon 30 and Kollidon VA 64 among the vinylpyrrolidone-based polymers will significantly suppress the formation of crystals for the compound of Formula 1.

Experimental Example 2: Confirmation of Whether a Crystal has been Precipitated after 24 Hours Storage of the Composition of Preparation Example 1

Figure 1:
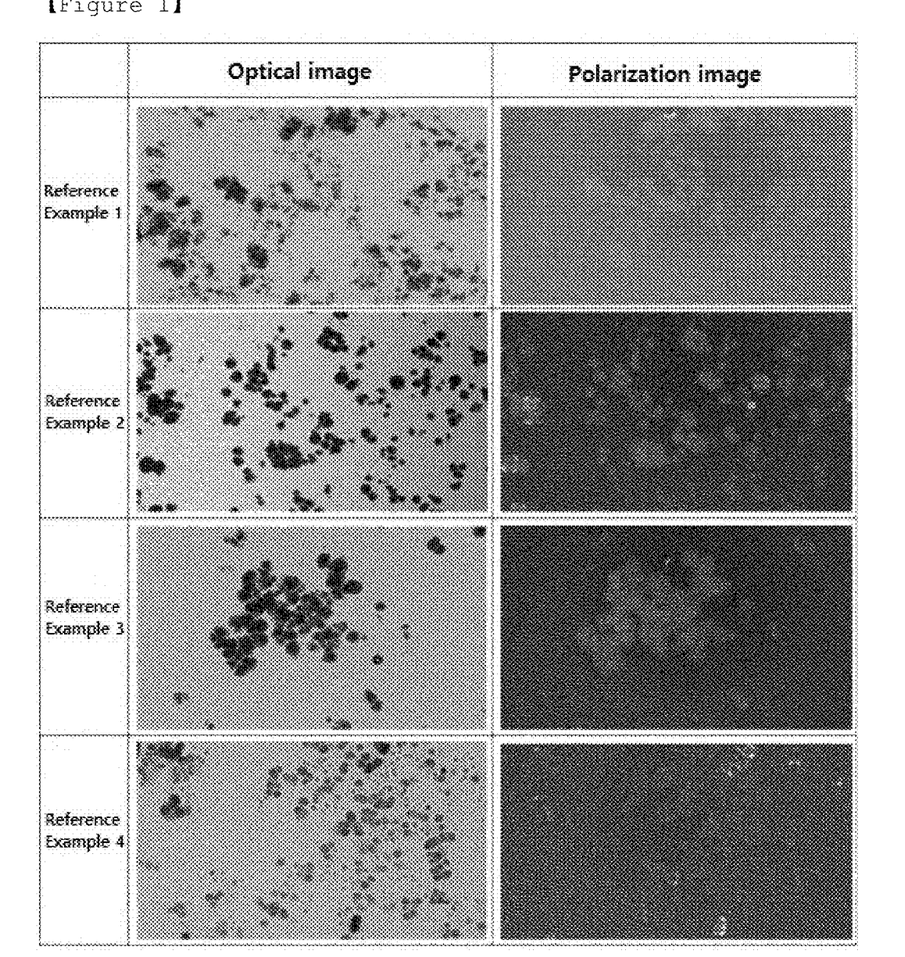
FIG. 1 is an optical and polarization microscope image observing whether crystals are precipitated after Reference Examples 1 to 4 of the embodiment of the invention were stored in a chamber at 40° C. for 24 hours, respectively.

After storing the compositions of Reference Examples 1 to 4 of the embodiment of the invention prepared in Preparation Example 1 in a chamber at 40° C. for 24 hours, whether or not crystals were precipitated was observed using an optical microscope and a polarizing filter (Olympus BX50 Microphotographic System, Tokyo, Japan), and the results are shown in FIG. 1.

Whether or not crystals were precipitated was judged as a crystal when irregular particles with dark color are observed in the image from the optical microscope, and at the same time, anisotropic particles are observed in the polarization image at the same position.

As can be seen in FIG. 1, it was confirmed that the precipitation of crystals was suppressed in all of Reference Examples 1 to 4 using a vinylpyrrolidone-based polymer. Particularly, it was confirmed that the precipitation of crystals is significantly suppressed in Reference Examples 2 and 4 of the embodiment of the invention using Kollidon 30 and Kollidon VA 64 as a vinylpyrrolidone-based polymer.

Experimental Example 3: Confirmation of the Stability of the Composition of Preparation Example 2

Figure 2A:
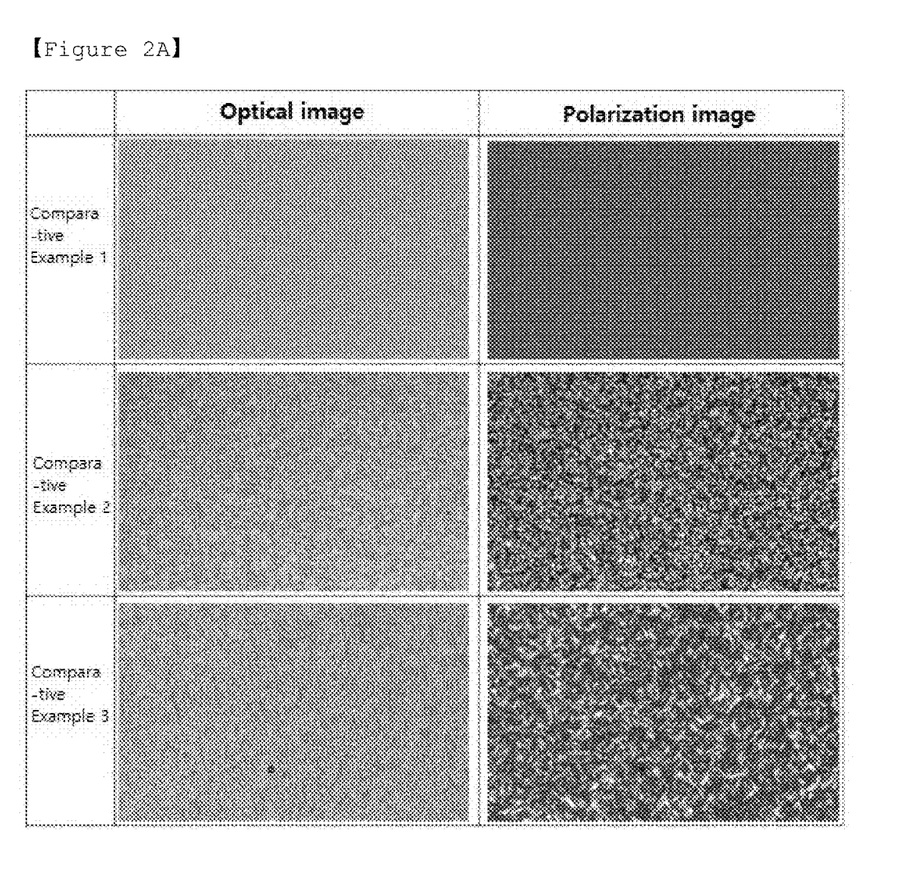
FIGS. 2A to 2C are optical and polarization microscope images observing whether crystals are precipitated after Comparative Examples 1 to 3 and Examples 1 to 7 of the embodiment of the invention were stored in a constant temperature chamber at 40° C., which is an accelerated condition, for 2 weeks.
Figure 2B:
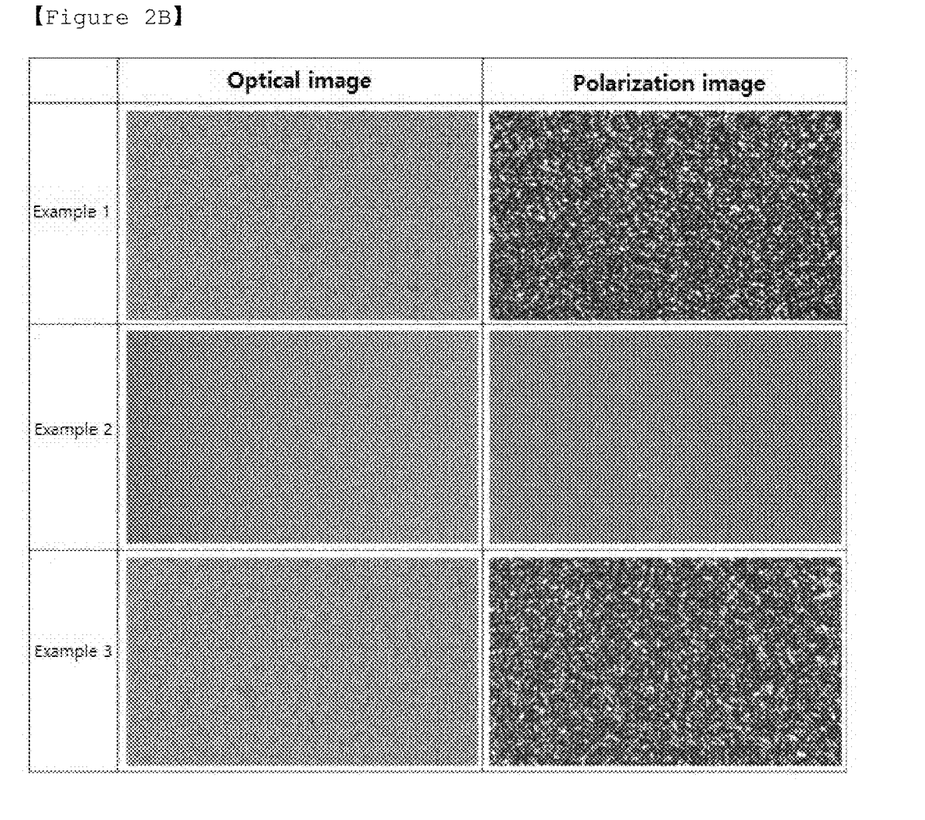
Figure 2C:
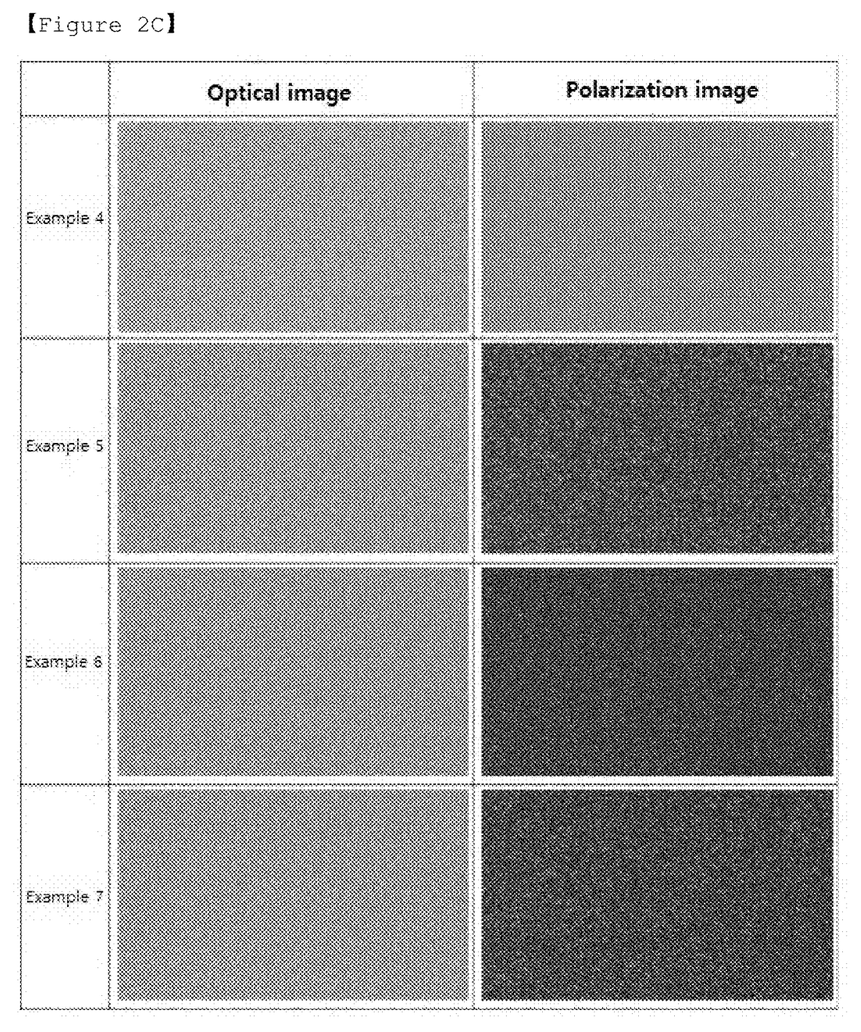

After the compositions of the creams containing the vinylpyrrolidone-based polymer prepared in Preparation Example 2 were stored for 2 weeks in a constant temperature chamber at 40° C., which is an accelerated condition, they were observed (100×) using an optical and polarization microscope, and the results are shown in FIGS. 2a to 2c.

As can be seen from FIGS. 2A to 2C, it was confirmed that in the case of Comparative Example 3, which contains the compound of Formula 1 and does not contain a vinylpyrrolidone-based polymer, crystals are precipitated when compared with Comparative Example 1, which does not contain the compound of Formula 1 and does not contain a vinylpyrrolidone-based polymer.

On the other hand, it was confirmed that in the case of Examples 1 and 3 using polyvinyl pyrrolidone such as Kollidon 17 or Kollidon 90, precipitation of crystals is suppressed when compared to Comparative Example 2, which does not contain the compound of Formula 1 and contains a vinylpyrrolidone-based polymer.

In addition, it can be seen that in the case of compositions (Examples 2 and 4) of the embodiment of the invention using Kollidon 30 or Kollidon VA 64 as a vinylpyrrolidone-based polymer, precipitation of crystals is significantly suppressed.

In addition, it can be seen that in the case of compositions (Examples 4 to 7) of the embodiment of the invention using the same amount of Kollidon VA 64 as a vinylpyrrolidone-based polymer, but using PEG300, PEG400, diethylene glycol monoethylether and DMSO, respectively, as a solvent, precipitation of crystals was also remarkably suppressed, and in particular, in the case of Example 4 using PEG400, the suppression effect on the precipitation of crystals was the best.

Figure 3:
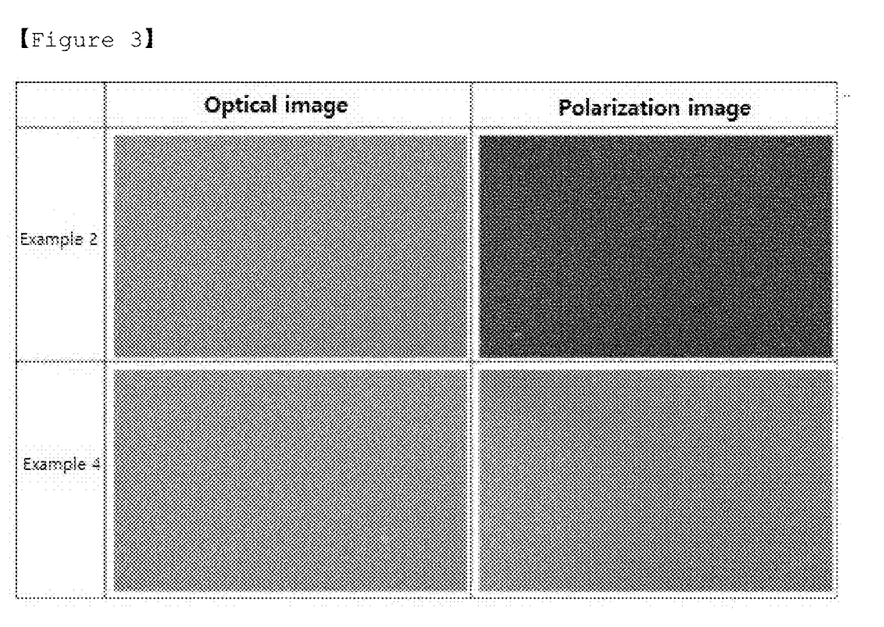
FIG. 3 is an optical and polarization microscope image observing whether crystals are precipitated after Examples 2 and 4 of the embodiment of the invention were stored in a constant temperature chamber at 40° C., which is a condition, for 8 months.

From subsequent observations, it was confirmed that in the case of Examples 2 and 4 compositions of the embodiment of the invention using Kollidon 30 and Kollidon VA 64, the formation of crystals was suppressed for more than 8 months in a constant temperature chamber at 40° C. (FIG. 3).

The invention claimed is:

1. A method for suppressing formation of crystals from a pharmaceutical composition comprising a mixed solution of a first solution comprising a compound of (R)-N-[1-(3,5-difluoro-4-methanesulfonamino-phenyl)-ethyl]-3-(2-propyl-6-trifluoromethyl-pyridin-3-yl)-acrylamide of the following Formula 1 and a second solution comprising a vinylpyrrolidone-based polymer and water, said method comprising a step of adding the second solution to the first solution to prepare the mixed solution, wherein the pharmaceutical composition is a dispersion solution comprising water, wherein the compound of Formula 1 is dispersed in the pharmaceutical composition, wherein the vinylpyrrolidone-based polymer has a K-value of 25 to 35, wherein the vinylpyrrolidone-based polymer is copovidone, and wherein a weight ratio of the vinylpyrrolidone-based polymer to the compound of Formula 1 is 1 to 3:1:

<Formula 1>

2. The method according to claim 1, wherein the vinylpyrrolidone-based polymer is contained in an amount of 1 to 5% by weight based on total weight of the pharmaceutical composition.

3. The method according to claim 1, wherein the pharmaceutical composition further comprises a solvent having a solubility for the compound of Formula 1 of 100 mg/mL or more.

4. The method according to claim 3, wherein the solvent is selected from the group consisting of diethylene glycol monoethylether, polyethylene glycol, 2-pyrrolidone, and dimethyl sulfoxide, or a combination thereof.

5. The method according to claim 4, wherein the solvent is diethylene glycol monoethylether, dimethyl sulfoxide, or polyethylene glycol.

6. The method according to claim 5, wherein the polyethylene glycol is polyethylene glycol 300 or polyethylene glycol 400.

7. The method according to claim 3, wherein the solvent is contained in an amount of 5 to 20% by weight based on total weight of the pharmaceutical composition.

8. The method according to claim 1, wherein the compound of Formula 1 is contained in an amount of 0.1 to 1.5% by weight based on total weight of the pharmaceutical composition.

9. The method according to claim 1, wherein the pharmaceutical composition is in the form of a topical pharmaceutical composition.

10. The method according to claim 1, wherein the pharmaceutical composition is in the form of a topical pharmaceutical composition selected from the group consisting of a cream, a gel, a patch, a spray, an ointment, a plaster, a lotion, a liniment, a paste, and a cataplasma formulation.

* * * * *